United States Patent
Lim et al.

(10) Patent No.: US 10,470,996 B2
(45) Date of Patent: Nov. 12, 2019

(54) COLLOID HAVING SELF-IONTOPHORESIS CAPACITY, PREPARATION METHOD THEREFOR, AND COSMETIC COMPOSITION CONTAINING SAME

(71) Applicants: AMOREPACIFIC CORPORATION, Seoul (KR); INDUSTRY-UNIVERSITY COOPERATION FOUNDATION HANYANG UNIVERSITY ERICA CAMPUS, Ansan-si Gyeonggi-do (KR)

(72) Inventors: Hyung Jun Lim, Yongin-si (KR); Yong Jin Kim, Yongin-si (KR); Jon Hwan Lee, Yongin-si (KR); Jin Woong Kim, Seongnam-si (KR); Ji Eun Kim, Ansan-si (KR)

(73) Assignees: AMOREPACIFIC CORPORATION, Seoul (KR); INDUSTRY-UNIVERSITY COOPERATION FOUNDATION HANYANG UNIVERSITY ERICA CAMPUS, Gyeonggi-Do (KR)

( * ) Notice: Subject to any disclaimer, the term of this patent is extended or adjusted under 35 U.S.C. 154(b) by 44 days.

(21) Appl. No.: 15/562,567

(22) PCT Filed: Mar. 28, 2016

(86) PCT No.: PCT/KR2016/003120
§ 371 (c)(1),
(2) Date: Sep. 28, 2017

(87) PCT Pub. No.: WO2016/159606
PCT Pub. Date: Oct. 6, 2016

(65) Prior Publication Data
US 2018/0110715 A1   Apr. 26, 2018

(30) Foreign Application Priority Data
Mar. 31, 2015   (KR) .................. 10-2015-0045037

(51) Int. Cl.
| | | |
|---|---|---|
| *A61K 8/02* | (2006.01) | |
| *A61K 8/04* | (2006.01) | |
| *A61K 8/81* | (2006.01) | |
| *A61K 8/87* | (2006.01) | |
| *A61Q 19/00* | (2006.01) | |

(52) U.S. Cl.
CPC ................. *A61K 8/87* (2013.01); *A61K 8/02* (2013.01); *A61K 8/0241* (2013.01); *A61K 8/0266* (2013.01); *A61K 8/044* (2013.01); *A61K 8/8123* (2013.01); *A61Q 19/00* (2013.01); *A61K 2800/412* (2013.01); *A61K 2800/413* (2013.01); *A61K 2800/614* (2013.01); *A61K 2800/624* (2013.01)

(58) Field of Classification Search
CPC .......... A61K 8/87; A61K 8/02; A61K 8/0241; A61K 8/0266; A61K 8/044; A61K 8/8123; A61Q 19/00
See application file for complete search history.

(56) References Cited

U.S. PATENT DOCUMENTS

| | | | |
|---|---|---|---|
| 2010/0330147 A1* | 12/2010 | Hossainy | |
| 2011/0082411 A1 | 4/2011 | Imran | |
| 2011/0160639 A1 | 6/2011 | Yanaki | |

FOREIGN PATENT DOCUMENTS

| | | |
|---|---|---|
| JP | 9286891 A | 11/1997 |
| JP | 201310704 A | 1/2013 |
| KR | 1020090098670 A | 9/2009 |
| KR | 2020100004529 U | 5/2010 |
| KR | 1020120057744 A | 6/2012 |
| KR | 1020120089397 A | 8/2012 |

OTHER PUBLICATIONS

International Search report for PCT/KR2016/003120, dated Jul. 25, 2016 (2 pages).
Extended European Search Report dated Oct. 12, 2018, 5 pp.

* cited by examiner

*Primary Examiner* — Alma Pipic
(74) *Attorney, Agent, or Firm* — Cantor Colburn LLP

(57) ABSTRACT

The present invention provides: a colloid having a self-iontophoresis capacity, comprising elastomer microparticles and a piezoelectric layer encompassing the same; a preparation method therefor; and a cosmetic composition containing the same.
According to the present invention, iontophoresis occurs by itself without the help of additional instruments, thereby allowing water-soluble active ingredients in a cosmetic composition to be effectively and transdermally delivered and absorbed.

19 Claims, 6 Drawing Sheets

COLLOID HAVING SELF-IONTOPHORESIS CAPACITY, PREPARATION METHOD THEREFOR, AND COSMETIC COMPOSITION CONTAINING SAME

CROSS-REFERENCE TO RELATED APPLICATION

This application claims the priority of Korean Patent Application No. 10-2015-0045037, filed on Mar. 31, 2015, and all the benefits accruing therefrom under 35 U.S.C. § 119, the contents of which in its entirety are herein incorporated by reference.

TECHNICAL FIELD

The present disclosure relates to a colloid having a self-iontophoresis capacity, a method for preparing the same, and a cosmetic composition including the same.

BACKGROUND

Although water-soluble active ingredients realize excellent effects in the skin, they have a fatal disadvantage in that they cannot be absorbed transdermally. Therefore, it is difficult for a cosmetic composition containing such ingredients to realize their effects in the skin. This is because the skin has a multilayer structure with a hydrophobic base. Such a skin barrier function to water-soluble active ingredients may be overcome by using cosmetic instruments. However, since consumers don't like inconvenience of using cosmetic instruments, approaches using cosmetic instruments have not been positioned adequately in the cosmetic market despite excellent performance. Therefore, there is a need for developing a novel technology capable of delivering water-soluble active ingredients effectively to the skin without the aid of cosmetic instruments.

In 2000's, transdermal absorption technologies using iontophoresis stared to be suggested. The key of such technologies is allowing electric current to flow on the skin surface to induce iontophoresis so that water-soluble drugs may be introduced to the skin along the electric current. It has been reported that macromolecules such as proteins as well as water-soluble low-molecular weight drugs can be delivered through the skin. It has been already determined clinically in the cosmetic field that cosmetic instruments realizing an iontophoresis capacity increases skin absorption of water-soluble active ingredients and show their unique effects in the skin. However, there is a disadvantage in that such effects can be realized only by using instruments.

Use of piezoelectricity allows electric current to flow with no external power supply. Particularly, piezoelectric devices have been used in various forms in the display industry. Such devices are characterized in that electric current flows at a pressurized portion when pressure is applied thereto (e.g. a touch screen). The devices are systems in which structural deformation of a piezoelectric layer between two electrodes forms an electric dipole to induce generation of electric current.

The above information disclosed in the Background section is only for enhancement of understanding of the background of the invention and it may therefore contain information that does not form the prior art that is already known to a person of ordinary skill in the art.

DISCLOSURE

Technical Problem

According to the present disclosure, it has been found that when a piezoelectric system is realized on a colloid and a cosmetic composition containing the colloid is used on the skin, two contacting skin sites function as electrodes to generate electric current autonomously, thereby enhancing transdermal absorption of a water-soluble active ingredient contained in the cosmetic composition. Therefore, a technical problem to be solved by the present disclosure is to provide a colloid having a self-iontophoresis capacity capable of effectively delivering a water-soluble active ingredient transdermally without the aid of an additional instrument, a method for preparing the same, and a cosmetic composition including the same.

Technical Solution

In one general aspect, there is provided a colloid having a self-iontophoresis capacity, which includes elastomer microparticles and a piezoelectric layer surrounding the elastomer microparticles.

According to an embodiment, the elastomer microparticle may be at least one selected from the group consisting of polyurethane, silicone gum, crosslinked acrylic polymer and natural rubber.

According to another embodiment, the piezoelectric layer may include a piezoelectric polymer.

According to still another embodiment, the piezoelectric layer may include a charged layer, a piezoelectric polymer layer and a polyelectrolyte layer.

According to still another embodiment, the piezoelectric polymer may be at least one selected from polyvinylidene fluoride and poly(vinylidene fluoride-trifluoroethylene) copolymer.

According to still another embodiment, the charged layer may include at least one selected from the group consisting of n-dodecylpyridinum chloride, linear diamine, linear alkylamine, cetyl trimethylammonium bromide, benzalkonium chloride, benzetonium chloride, cetrimonium chloride, alkyltrimethylammonium chloride, dialkyldimethyl ammonium chloride, imidazole, glyceride sulfate, dodecylbenzene sulfonate, lignosulfonate salt, sarcoside, sodium dodecylsulfonate, sulfocarboxyl compound, alkylether sulfate, alkyl sulfate, alpha-olefin sulfonate, organic phosphate-based surfactant, potassium cocoyl glycinate and alkanol amide sulfate.

According to still another embodiment, the polyelectrolyte layer may include at least one selected from the group consisting of diethylaminoethyl methacrylate, diethylaminoethyl acrylate, polyvinylpyridines, polyacrylamide, polyethyleneimine, carboxymethyl cellulose, polyglutamic acid, polyvinyl amine, polysodium styrene sulfonate and polyacrylic acid.

According to still another embodiment, the elastomer microparticles may have a diameter of 10-50 μm.

According to yet another embodiment, the piezoelectric polymer may be nanoparticles having a diameter of 10-800 nm.

In another general aspect, there is provided a method for preparing the colloid, including the steps of:
  forming elastomer microparticles; and
  coating the elastomer microparticles with a piezoelectric layer to form piezoelectric elastomer microparticles.

According to an embodiment, the step of forming the elastomer microparticles may include the steps of:

preparing emulsion droplets from a solution containing an elastomer precursor and a photoinitiator;

removing the solvent from the emulsion droplets; and carrying out photopolymerization of the emulsion droplets from which the solvent is removed to form the elastomer microparticles.

According to another embodiment, the method may further include a step of adding an ionomer so that the surface of the elastomer microparticles may be anionically charged.

According to still another embodiment, the step of preparing the emulsion droplets may use a microfluidic process.

According to still another embodiment, the step of removing the solvent may be carried out by evaporation of the solvent under reduced pressure.

According to still another embodiment, the step of coating the elastomer microparticles with a piezoelectric layer to form piezoelectric elastomer microparticles may include the steps of:

coating the elastomer microparticles with a charged layer; and applying a piezoelectric polymer layer onto the charged layer.

According to still another embodiment, the method may further include a step of applying a polyelectrolyte layer onto the piezoelectric polymer layer.

According to still another embodiment, the step of applying a piezoelectric polymer layer may be carried out by using piezoelectric polymer nanoparticles formed by precipitating a polar piezoelectric polymer solution in an aqueous surfactant solution.

According to still another embodiment, the piezoelectric polymer nanoparticles may have a diameter of 10-800 nm.

According to still another embodiment, the piezoelectric polymer nanoparticles may have a surface charge of 10-60 mV.

In still another general aspect, there is provided a cosmetic composition for self-iontophoretic transdermal absorption, which includes the colloid.

According to an embodiment, the cosmetic composition may include a water-soluble active ingredient.

According to another embodiment, the cosmetic composition generates electric current on the skin without the aid of an additional instrument to perform self-iontophoresis.

Advantageous Effects

According to the colloid having a self-iontophoresis capacity, method for preparing the same and the cosmetic composition including the same disclosed herein, it is possible to carry out iontophoresis autonomously without the aid of an additional instrument so that the water-soluble active ingredient in the cosmetic composition may be effectively delivered and absorbed transdermally.

BEST MODE

Figure 1:
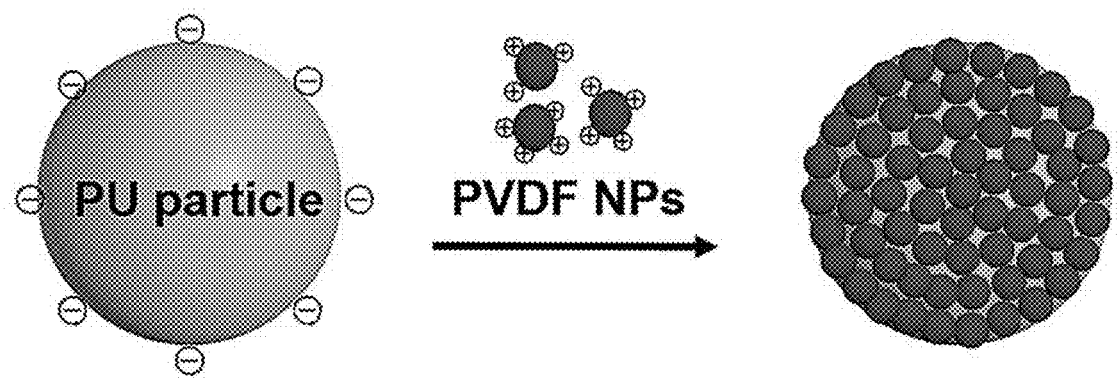
FIG. 1 is a schematic view illustrating the process for preparing piezoelectric elastomer microparticles according to an embodiment.

Exemplary embodiments now will be described more fully hereinafter. This disclosure may, however, be embodied in many different forms and should not be construed as limited to the exemplary embodiments set forth therein.

In one aspect, there is provided a colloid having a self-iontophoresis capacity, which includes elastomer microparticles and a piezoelectric layer surrounding the elastomer microparticles.

Although the elastomer microparticles are not particularly limited, the elastomer microparticle may be at least one elastomer selected from the group consisting of polyurethane (PU), silicone gum, crosslinked acrylic polymer and natural rubber, particularly polyurethane. For example, polyurethane is proper, since it has biocompatibility.

The elastomer microparticles may have a diameter of 10-50 μm, particularly 10-20 μm. When the elastomer microparticles have a diameter less than 10 μm, it is not easy to apply a PVDF coating layer onto the particles, a degree of particle deformation of elastomer is decreased and a possibility of generating electric current is reduced. When the elastomer microparticles have a diameter larger than 50 μm, a feeling of irritation may occur in a cosmetic formulation.

According to an embodiment, the surface of elastomer microparticles is coated with a piezoelectric layer so that the surface of elastomer microparticles may generate electric current through deformation.

The piezoelectric layer may include a piezoelectric polymer.

Although the piezoelectric polymer is not particularly limited, it may be at least one selected from polyvinylidene fluoride and poly(vinylidene fluoride-trifluoroethylene) copolymer, preferably polyvinylidene fluoride (PVDF).

For example, polyvinylidene fluoride is proper, since it realizes biocompatibility and piezoelectricity at the same time.

The piezoelectric polymer may be nanoparticles having a diameter of 10-800 nm, particularly 10-100 nm. When the piezoelectric polymer has a diameter less than 10 nm, it cannot be prepared with ease. When the piezoelectric polymer has a diameter larger than 800 nm, it is not easy to carry out surface coating on the elastomer microparticles.

According to another embodiment, the piezoelectric layer may be a piezoelectric polymer layer including the piezoelectric polymer.

In addition, the piezoelectric layer may include a charged layer coated on the elastomer microparticles and a piezoelectric polymer layer coated on the charged layer.

In addition, the piezoelectric layer may include a charged layer coated on the elastomer microparticles, a piezoelectric polymer layer coated on the charged layer, and a polyelectrolyte layer coated on the piezoelectric polymer layer.

The charged layer may include at least one selected from the group consisting of cationic surfactants, such as n-dodecylpyridinum chloride, linear diamine, linear alkylamine, cetyl trimethylammonium bromide, benzalkonium chloride, benzetonium chloride, cetrimonium chloride, alkyltrimethylammonium chloride, dialkyldimethyl ammonium chloride and imidazole, and anionic surfactants, such as glyceride sulfate, dodecylbenzene sulfonate, lignosulfonate salt, sarcoside, sodium dodecylsulfonate, sulfocarboxyl compounds, alkylether sulfate, alkyl sulfate, alpha-olefin sulfonate, organic phosphate-based surfactants, potassium cocoyl glycinate and alkanol amide sulfate. The charged layer is attached to the surface of the negatively charged elastomer microparticles.

For example, the surfactant may be hexadecyltrimethylammonium bromide (CTAB) or sodium dodecyl sulfate (SDS).

The polyelectrolyte layer may include, as a cationic polymer, at least one selected from the group consisting of diethylaminoethyl methacrylate, diethylaminoethyl acrylate, polyvinylpyridines, polyacrylamide, polyethyleneimine, carboxymethyl cellulose, polyglutamic acid, polyvinyl amine, polysodium styrene sulfonate and polyacrylic acid.

The polyelectrolyte layer may function as a surface protection film.

The colloid including elastomer microparticles and a piezoelectric layer surrounding the elastomer microparticles has a self-iontophoresis capacity. The piezoelectric elastomer microparticles can be deformed and the deformation thereof occurs autonomously due to the shear stress applied between the skin sites. In addition, the surface of the piezoelectric elastomer microparticles can generate electric current through the deformation.

The colloid having a self-iontophoresis capacity may be obtained by the following method.

In other words, in another aspect, there is provided a method for preparing a colloid, including the steps of:

forming elastomer microparticles; and coating the elastomer microparticles with a piezoelectric layer to form piezoelectric elastomer microparticles.

Hereinafter, the method for preparing the above-mentioned colloid having a self-iontophoresis capacity will be explained in detail.

First, elastomer microparticles are formed.

According to an embodiment, the step of forming the elastomer microparticles may include the steps of:

preparing emulsion droplets from a solution containing an elastomer precursor and a photoinitiator;

removing the solvent from the emulsion droplets; and carrying out photopolymerization of the emulsion droplets from which the solvent is removed to form the elastomer microparticles.

In addition, the method may further include a step of adding an ionomer so that the surface of the formed elastomer microparticles may be anionically charged.

Although there is no particular limitation, the step of preparing emulsion droplets from a solution containing an elastomer precursor and a photoinitiator may be carried out by using a microfluidic process.

As described above, the elastomer may be at least one selected from the group consisting of polyurethane, silicone gum, crosslinked acrylic polymer and natural rubber. Thus, the elastomer precursor may be a polyurethane precursor, silicone gum precursor, crosslinked acrylic polymer precursor and natural rubber precursor.

The polyurethane precursor may include an isocyanate (hard segment): hexamethylene diisocyanate, 4,4-dicyclohexylmethane diisocyanate, 1,4-tetramethylene diisocyanate, isophorone diisocyanate, 1,4-cyclohexane diisocyanate, toluene-2,4-diisocyanate, toluene-2,6-diisocyanate, 4-methoxy-1,3-phenylene diisocyanate; and a polyol (soft segment): ethylene glycol, propylene glycol, butanediol, 1,6-hexanediol, glycerol, trimethylol propane, neopentyl glycol, polyethylene glycol, polypropylene glycol, polyethylenepropylene glycol, polytetramethylene glycol, polycarbonate polyol, polycaprolactone polyol, polyester polyol, polyether polyol, fatty acid-modified polyester polyol, and fatty acid-modified polyether polyol.

Although the photoinitiator is not particularly limited, it may be at least one selected from benzoin ether-, benzophenone-, acetophenone- and thioxanthone-based photoinitiators.

The solution containing the elastomer precursor and photoinitiator may include a volatile solvent. The volatile solvent is not particularly limited but may include toluene, chloroform, or the like.

Although the step of removing the solvent from the emulsion droplets is not particularly limited, it may be carried out by evaporation under reduced pressure. Particularly, the solvent may be evaporated at 30-60° C., particularly 40-50° C. When the solvent is removed from the emulsion droplets, only the elastomer precursor and photoinitiator remain.

In addition, the step of carrying out photopolymerization of the emulsion droplets from which the solvent is removed to form elastomer microparticles may be photopolymerization under UV irradiation. For example, the photopolymerization may be carried out by irradiating UV-A at about 2000 mJ/cm$^2$ for about 1 minute, but is not limited thereto. The elastomer precursor is converted into an elastomer by the photopolymerization.

Then, an ionomer may be added so that the surface of the formed elastomer microparticles may be anionically charged.

Although the ionomer is not particularly limited, it may include a water-dispersible urethane acrylate ionomer. The water-dispersible urethane acrylate ionomer may include: an isocyanate (hard segment): hexamethylene diisocyanate, 4,4-dicyclohexylmethane diisocyanate, 1,4-tetramethylene diisocyanate, isophorone diisocyanate, 1,4-cyclohexane diisocyanate, toluene-2,4-diisocyanate, toluene-2,6-diisocyanate, 4-methoxy-1,3-phenylene diisocyanate; a polyol (soft segment): ethylene glycol, propylene glycol, butanediol, 1,6-hexanediol, glycerol, trimethylol propane, neopentyl glycol, polyethylene glycol, polypropylene glycol, polyethylenepropylene glycol, polytetramethylene glycol, polycarbonate polyol, polycaprolactone polyol, polyester polyol, polyether polyol, fatty acid-modified polyester polyol, and fatty acid-modified polyether polyol; and a hydrophilic monomer: dimethylol propionic acid, dimethylol butanoic acid, carboxyl group-containing polycaprolactonediol, polyethylene glycol, polypropylene glycol, polyethylenepropylene glycol, polyether-1,3-diol, polyethylene glycol methyl ether; hydroxyl (meth)acrylate, hydroxyethyl methacrylate, hydroxyethyl acrylate, hydroxypropyl acrylate, hydroxypropyl methacrylate, hydroxybutyl acrylate, hydroxybutyl methacrylate, pentaerythritol triacrylate, and dipentaerythritol acrylate.

After the elastomer microparticles are formed as described above, they are coated with a piezoelectric layer to form piezoelectric elastomer microparticles. Herein, layer-by-layer (L-b-L) deposition technology is used for the purpose of coating with the piezoelectric layer.

The step of coating the elastomer microparticles with a piezoelectric layer to form piezoelectric elastomer microparticles may include the steps of:

coating the elastomer microparticles with a charged layer; and applying a piezoelectric polymer layer onto the charged layer.

The method may further include a step of applying a polyelectrolyte layer onto the piezoelectric polymer layer.

The step of applying a piezoelectric polymer layer may be carried out by using piezoelectric polymer nanoparticles formed by precipitating a polar piezoelectric polymer solution in an aqueous surfactant solution.

Although the solvent used for the polar piezoelectric polymer solution is not particularly limited, it may be methanol, ethanol, water, dimethyl acetamide, dimethyl formamide, acetone, chloroform, toluene, tetrahydrofuran, or the like.

The prepared piezoelectric polymer nanoparticles may have a diameter of 10-800 nm.

In addition, the piezoelectric polymer nanoparticles may have a surface charge of 10-60 mV. When the surface charge is less than 10 mV, it is not easy to carry out adsorption and coating on the surface of the elastomer microparticles. In addition, since the nanoparticles have a positive (+) surface potential due to the surfactant but the material to be coated actually is polyvinylidene fluoride (PVDF), or the like, the use of a surfactant for preparing nanoparticles is limited and thus the maximum surface charge is 60 mV.

Figure 4:
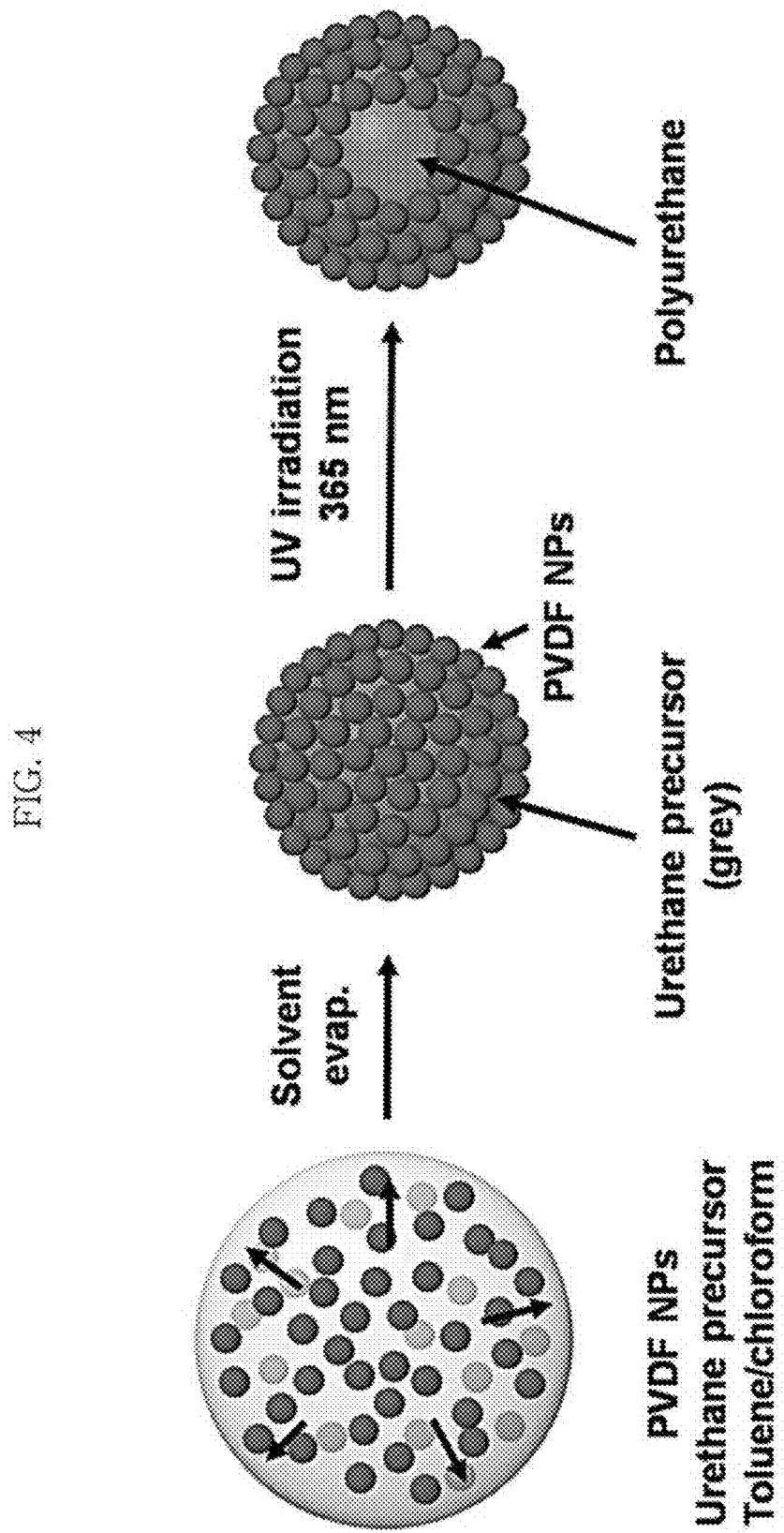
FIG. 4 is a schematic view illustrating the process for preparing piezoelectric particles using emulsion formation during the preparation of the elastomer microparticles according to an embodiment.

The piezoelectric capacity of the colloid having a self-iontophoresis capacity may be determined by measuring the amount of electric current generated depending on the pressure applied from a predetermined direction, after positioning the colloid particles between two electrodes (ITO glass). Herein, the piezoelectricity measuring system as shown in FIG. 4 may be used.

In still another aspect, there is provided a cosmetic composition for self-iontophoretic transdermal absorption, which includes the colloid.

In still another aspect, there is provided a method for enhancing transdermal absorption, which includes applying the colloid or the cosmetic composition for self-iontophoretic transdermal absorption including the same to a subject in need thereof.

In still another aspect, there is provided use of the colloid for the preparation of a cosmetic composition for self-iontophoretic transdermal absorption including the colloid.

In yet another aspect, there is provided the colloid for use in enhancing to transdermal absorption.

The cosmetic composition may include a water-soluble active ingredient. The water-soluble active ingredient is not particularly limited but particular examples thereof may include alpha-hydroxyl acid, polyhydroxy alkanoate, threhalose, propolis, saponine, or the like.

The cosmetic composition may include the water-soluble active ingredient in an amount of 30-70 wt %, particularly 40-60 wt %, based on the total weight of the composition.

According to the related art, a water-soluble active ingredient cannot be absorbed transdermally. However, it is possible to accomplish transdermal absorption of a water-soluble active ingredient easily and effectively by using the self-iontophoresis colloid disclosed herein.

The cosmetic composition including the colloid having a self-iontophoresis capacity generates electric current on the skin without the aid of an additional instrument to perform self-iontophoresis. Therefore, the present disclosure provides a novel formulation which allows more effective use of a water-soluble active ingredient in a cosmetic composition. Thus, an additional effect on the skin can be expected through the micro-current generated from the self-iontophoretic colloid.

EXAMPLE 1

1.1 Preparation of Elastomer Microparticles

A polyurethane precursor was dissolved in toluene and chloroform as solvents and then subjected to a microfluidic process to obtain mono-dispersed to emulsion droplets. The solvent obtained after recovering the mono-dispersed droplets was removed by evaporation under reduced pressure at 45° C. Then, UV-A was irradiated at 2000 mJ/cm$^2$ for about 1 minute to carry out photopolymerization so that the polyurethane precursor may be converted into a polyurethane elastomer. A polyurethane ionomer was introduced in a small amount (approximately 2 wt %) so that the surface of polyurethane microparticles may be anionically charged. The process is shown in FIG. 1 schematically.

1-2. Introduction of Piezoelectric Layer

Figure 2:
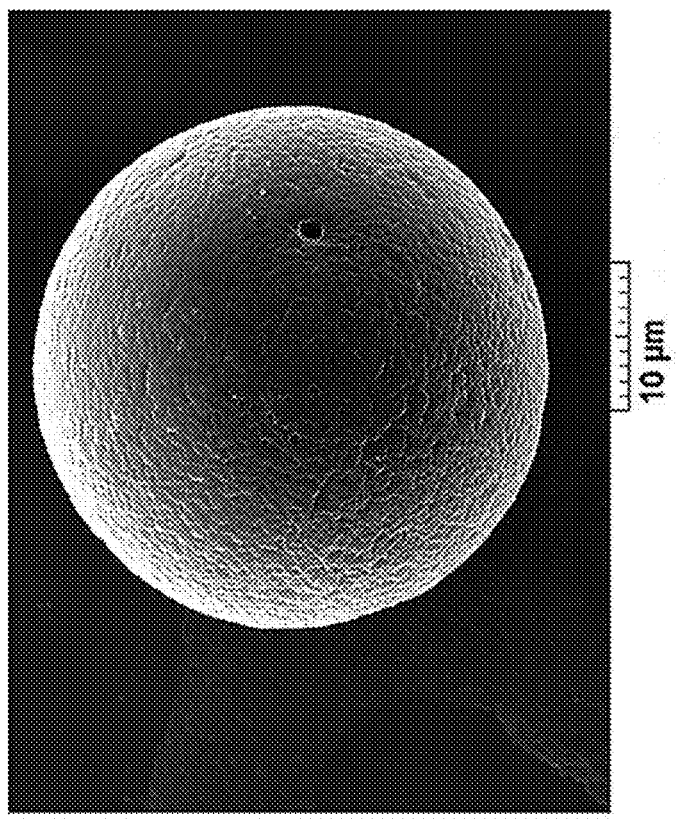
FIG. 2 is a scanning electron microscopic (SEM) image of the piezoelectric particles in the piezoelectric layer according to an embodiment.
Figure 2:
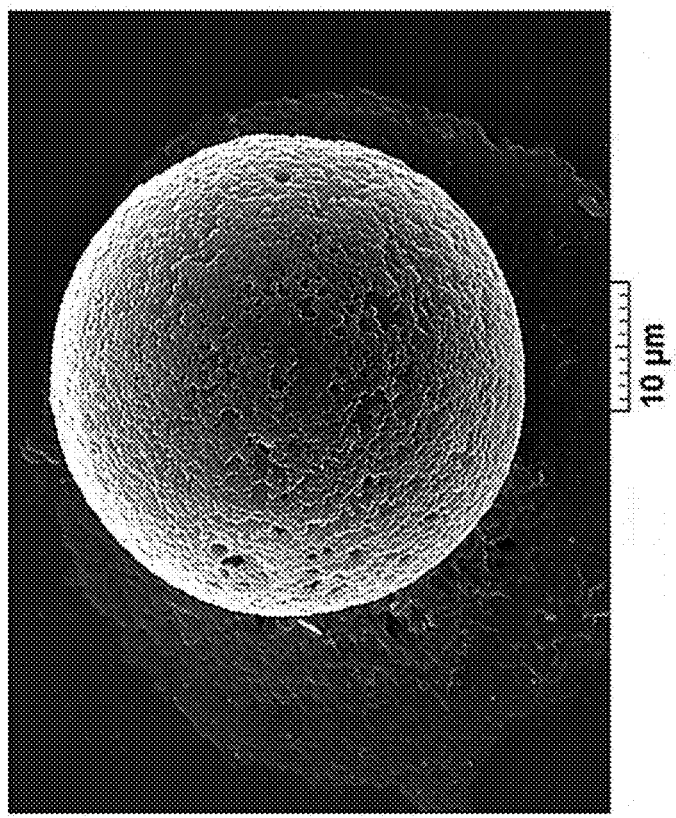

To a solution containing a surfactant (hexadecyltrimethylammonium bromide (CTAB) or sodium dodecyl sulfate (SDS)) and polyvinylidene fluoride (PVDF) dissolved therein, water was added dropwise to obtain polyvinylidene fluoride (PVDF) nanoparticles. The polyvinylidene fluoride (PVDF) nanoparticles were agitated together with the polyurethane elastomer to introduce a piezoelectric layer. The resultant piezoelectric particles are shown in FIG. 2 in the form of their SEM image.

1-3. Preparation of Piezoelectric Particles Using W/O/W Dual Emulsion Template

Figure 3A:
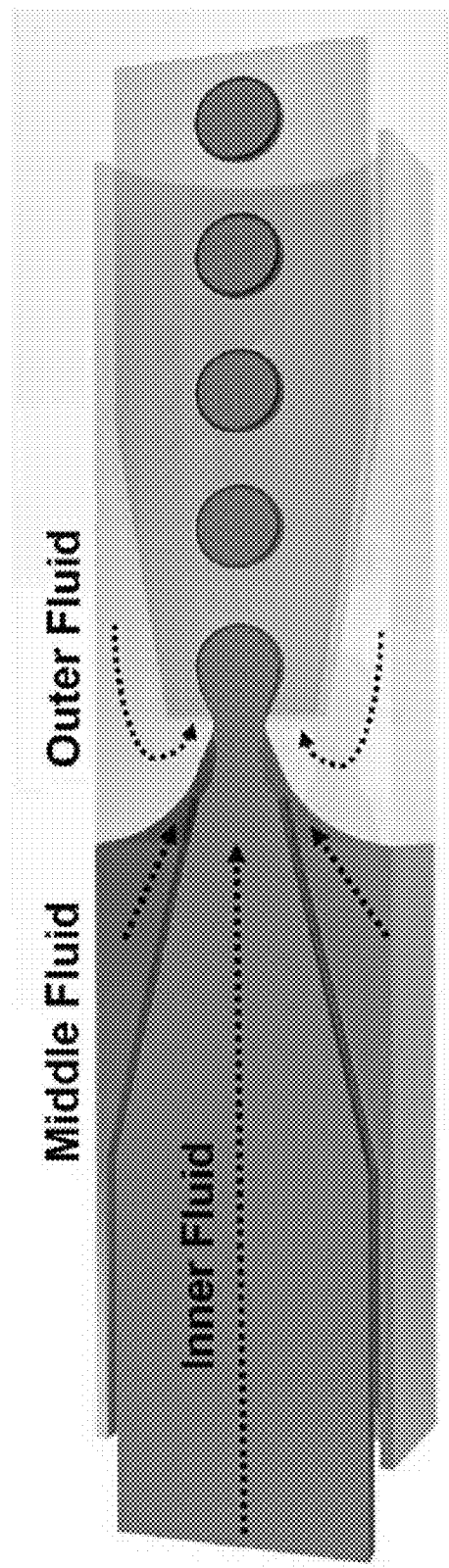
FIG. 3 shows a schematic view illustrating the preparation of dual emulsion droplets using a microfluidic process (FIG. 3A), an optical microscopic image of the piezoelectric particles obtained after photopolymerization (FIG. 3B), and a SEM image thereof during the preparation of the elastomer microparticles according to an embodiment (FIG. 3C).
Figure 3B:
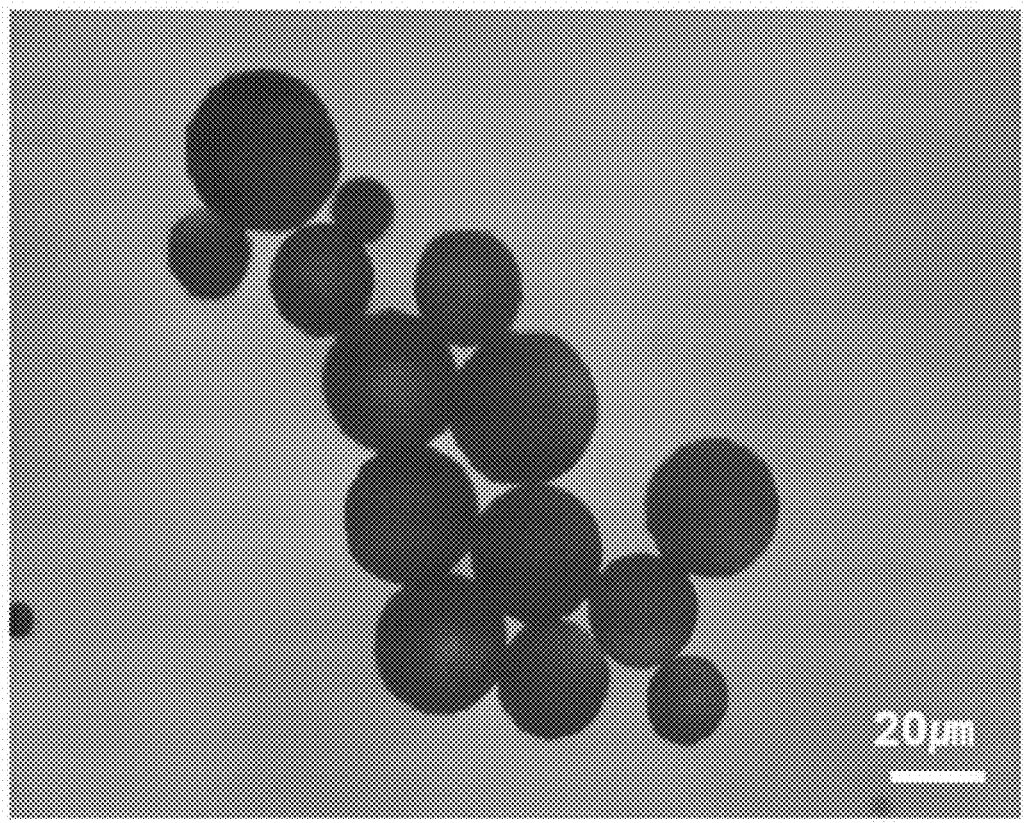
Figure 3C:
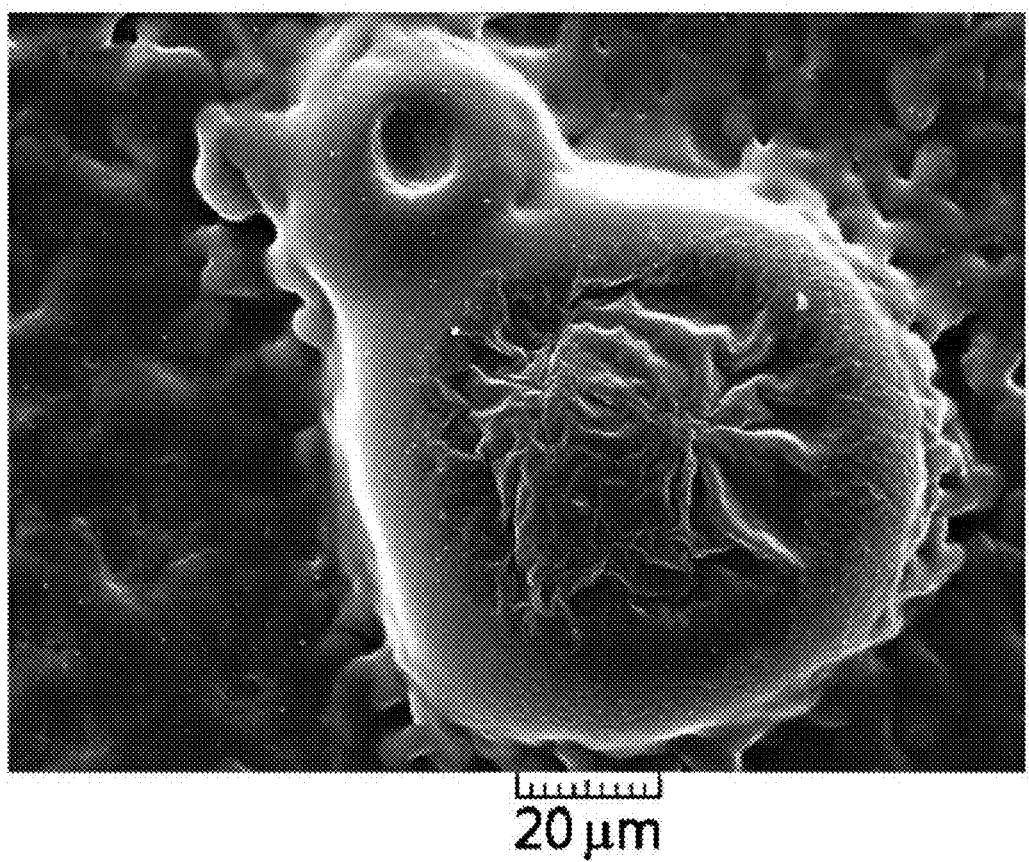

An aqueous solution of crosslinked acrylic polymer was used as inner fluid, and the polyvinylidene fluoride (PVDF) nanoparticles and polyurethane precursor dissolved in toluene and chloroform as solvents were used as middle fluid to obtain mono-dispersed dual emulsion droplets through a microfluidic process. The solvent obtained after recovering the mono-dispersed droplets was removed by evaporation under reduced pressure at 45° C. Then, UV-A was irradiated at 2000 mJ/cm$^2$ for about 1 minute to carry out photopolymerization of the crosslinked acrylic polymer. FIG. 3 shows a schematic view illustrating the preparation of dual emulsion droplets using a microfluidic process (FIG. 3A), an optical microscopic image of the piezoelectric particles obtained after photopolymerization (FIG. 3B), and a SEM image thereof during the preparation of the elastomer microparticles according to an embodiment (FIG. 3C).

1-4. Preparation of Piezoelectric Particles Using Emulsion Preparation

Polyvinylidene fluoride (PVDF) nanoparticles and a polyurethane precursor were dissolved in toluene and chloroform as solvents and emulsion droplets were prepared in an aqueous polyvinyl alcohol solution. The solvent obtained after recovering the mono-dispersed droplets was removed by evaporation under reduced pressure at 45° C. Then, UV-A was irradiated at 2000 mJ/cm$^2$ for about 1 minute to carry out photopolymerization so that the polyurethane precursor may be converted into a polyurethane elastomer. The process is shown in FIG. 4 schematically.

The invention claimed is:

1. A colloid having a self-iontophoresis capacity, which comprises elastomer microparticles and a piezoelectric layer surrounding the elastomer microparticles, wherein the piezoelectric layer comprises a charged layer and a piezoelectric polymer layer including a piezoelectric polymer.

2. The colloid according to claim 1, wherein the elastomer microparticle is at least one selected from the group consisting of polyurethane, silicone gum, crosslinked acrylic polymer, and natural rubber.

3. The colloid according to claim 1, wherein the piezoelectric layer further comprises a polyelectrolyte layer.

4. The colloid according to claim 1, wherein the piezoelectric polymer is at least one selected from polyvinylidene fluoride and poly(vinylidene fluoride-trifluoroethylene)copolymer.

5. The colloid according to claim 1, wherein the charged layer comprises at least one selected from the group consisting of n-dodecylpyridinum chloride, linear alkylamine, cetyl trimethylammonium bromide, benzalkonium chloride, benzetonium chloride, cetrimonium chloride, alkyltrimethylammonium chloride, dialkyldimethyl ammonium chloride, imidazole, glyceride sulfate, dodecylbenzene sulfonate, lignosulfonate salt, sarcoside, sodium dodecylsulfonate, sulfocarboxyl compounds, alkylether sulfate, alkyl sulfate, alpha-olefin sulfonate, organic phosphate-based surfactant, potassium cocoyl glycinate, and alkanol amide sulfate.

6. The colloid according to claim 3, wherein the polyelectrolyte layer comprises at least one selected from the group consisting of diethylaminoethyl methacrylate, diethylaminoethyl acrylate, polyvinylpyridines, polyacrylamide, polyethyleneimine, carboxymethyl cellulose, polyglutamic acid, polyvinyl amine, polysodium styrene sulfonate, and polyacrylic acid.

7. The colloid according to claim 1, wherein the elastomer microparticles have a diameter of 10-50 µm.

8. The colloid according to claim 1, wherein the piezoelectric polymer is in the form of nanoparticles having a diameter of 10-800 nm.

9. A method for preparing the colloid as defined in claim 1, which comprises the steps of:
    forming elastomer microparticles; and
    coating the elastomer microparticles with a piezoelectric layer to form piezoelectric elastomer microparticles.

10. The method for preparing the colloid according to claim 9, which further comprises a step of adding an ionomer to the surface of the elastomer microparticles to form an anionically charged surface.

11. The method for preparing the colloid according to claim 9, wherein the step of forming the elastomer microparticles comprises the steps of:
    preparing emulsion droplets from a solution comprising a solvent, an elastomer precursor, and a photoinitiator;
    removing or evaporating the solvent from the emulsion droplets; and
    carrying out photopolymerization of the emulsion droplets from which the solvent is removed to form the elastomer microparticles.

12. The method for preparing the colloid according to claim 11, wherein the step of preparing the emulsion droplets uses a microfluidic process.

13. The method for preparing the colloid according to claim 9, wherein the step of coating the elastomer microparticles with a piezoelectric layer to form piezoelectric elastomer microparticles comprises the steps of:
    coating the elastomer microparticles with a charged layer; and
    applying a piezoelectric polymer layer onto the charged layer.

14. The method for preparing the colloid according to claim 13, which further comprises a step of applying a polyelectrolyte layer onto the piezoelectric polymer layer.

15. The method for preparing the colloid according to claim 13, wherein the step of applying a piezoelectric polymer layer is carried out by using piezoelectric polymer nanoparticles formed by precipitating a polar piezoelectric polymer solution in an aqueous surfactant solution.

16. The method for preparing the colloid according to claim 15, wherein the piezoelectric polymer nanoparticles have a diameter of 10-800 nm, or have a surface charge of 10-60 mV.

17. A cosmetic composition for self-iontophoretic transdermal absorption, which comprises the colloid as defined in claim 1.

18. The cosmetic composition according to claim 17, which comprises a water-soluble active ingredient.

19. The cosmetic composition according to claim 17, which is capable of generating an electric current on the skin without the aid of an additional instrument to perform self-iontophoresis.

* * * * *